(12) United States Patent
Spector et al.

(10) Patent No.: US 12,635,670 B2
(45) Date of Patent: *May 26, 2026

(54) PET HARNESS FOR MONITORING BODY TEMPERATURE AND PROVIDING COOLING OR HEATING

(71) Applicant: Nicole Cafazzo Spector, Raleigh, NC (US)

(72) Inventors: Greyson Evan Spector, Raleigh, NC (US); Cole Garrett Spector, Raleigh, NC (US); Cade Wolfram Spector, Raleigh, NC (US); Sawyer Beckett Spector, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/066,831

(22) Filed: Feb. 28, 2025

(65) Prior Publication Data

US 2025/0194567 A1      Jun. 19, 2025

Related U.S. Application Data

(63) Continuation of application No. 16/597,178, filed on Oct. 9, 2019, now Pat. No. 12,250,926.
(Continued)

(51) Int. Cl.
*A01K 27/00* (2006.01)
*A01K 13/00* (2006.01)
(Continued)

(52) U.S. Cl.
CPC .......... *A01K 27/002* (2013.01); *A01K 13/006* (2013.01); *A61B 5/01* (2013.01);
(Continued)

(58) Field of Classification Search
CPC ........................... A01K 27/002; A01K 13/006
(Continued)

(56) References Cited

U.S. PATENT DOCUMENTS 3,916,911 A      11/1975  Sauder et al.
5,243,706 A       9/1993  Frim et al.
(Continued)

FOREIGN PATENT DOCUMENTS

CN          104013243 A      9/2014
CN          204653371 U      9/2015
(Continued)

OTHER PUBLICATIONS

Knapp, "How to Pick the Most Breathable Fabrics," REI Co-op: 7 pages (2002) Retrieved on Nov. 28, 2022, retrieved from <URL: www.rei.com/learn/expert-advice/how-to-pick-the-most-breathable-fabrics.html >.
(Continued)

*Primary Examiner* — David J Parsley
*Assistant Examiner* — Angelica Alejandra Almeida Bonnin
(74) *Attorney, Agent, or Firm* — KDW FIRM PLLC

(57) ABSTRACT

A harness for heating and/or cooling a wearer (e.g., a pet) of the harness includes an outer cover including a harness neck strap and a harness chest strap for securing the harness about the wearer of the harness, an internal surface having a breathable fabric material, at least one sensor attached to the harness chest strap, a thermal control device that cools or heats the wearer of the harness, a controller to activate the thermal control device, and straps arranged over an external surface of the outer cover.

20 Claims, 3 Drawing Sheets

Related U.S. Application Data

(60) Provisional application No. 62/743,960, filed on Oct. 10, 2018.

(51) Int. Cl.

| | |
|---|---|
| *A61B 5/00* | (2006.01) |
| *A61B 5/01* | (2006.01) |
| *A61B 5/145* | (2006.01) |
| *A61F 7/00* | (2006.01) |
| *A61B 5/024* | (2006.01) |
| *A61B 5/08* | (2006.01) |
| *A61F 7/02* | (2006.01) |
| *H04Q 9/00* | (2006.01) |

(52) U.S. Cl.
 CPC ........ *A61B 5/14542* (2013.01); *A61B 5/6805* (2013.01); *A61F 7/00* (2013.01); *A61F 7/0085* (2013.01); *A61B 5/02438* (2013.01); *A61B 5/0816* (2013.01); *A61B 2503/40* (2013.01); *A61F 2007/0018* (2013.01); *A61F 2007/0064* (2013.01); *A61F 2007/0065* (2013.01); *A61F 2007/0093* (2013.01); *A61F 2007/0094* (2013.01); *A61F 2007/0233* (2013.01); *H04Q 9/00* (2013.01)

(58) Field of Classification Search
 USPC ........................................................ 119/850
 See application file for complete search history.

(56) References Cited

U.S. PATENT DOCUMENTS

| | | | | |
|---|---|---|---|---|
| 5,353,793 | A | 10/1994 | Bornn | |
| 5,537,954 | A | 7/1996 | Beeghly et al. | |
| 6,649,873 | B1 | 11/2003 | Cintron et al. | |
| 7,120,938 | B2 | 10/2006 | Ichigaya | |
| 7,602,302 | B2 | 10/2009 | Hokuf et al. | |
| 7,816,632 | B2 | 10/2010 | Bourke et al. | |
| 9,332,734 | B1 | 5/2016 | Hege | |
| 9,936,680 | B2 | 4/2018 | Womble et al. | |
| 9,956,112 | B2 | 5/2018 | Van Oudenallen et al. | |
| 10,034,456 | B2 | 7/2018 | Pomponio | |
| 10,231,433 | B1 * | 3/2019 | Caruso | A01K 13/006 |
| 10,440,938 | B2 | 10/2019 | Menkes et al. | |
| 10,624,314 | B2 * | 4/2020 | Lui | A01K 13/006 |
| 10,674,708 | B2 | 6/2020 | Beck | |
| 10,874,089 | B2 * | 12/2020 | Hurley | A61B 5/0022 |
| 11,000,406 | B2 | 5/2021 | Thomas et al. | |
| 11,224,380 | B2 * | 1/2022 | Alnofeli | A61B 5/0205 |
| 11,330,797 | B2 | 5/2022 | Couse et al. | |
| 11,490,598 | B2 * | 11/2022 | Belhomme | G01S 1/68 |
| 2005/0284416 | A1 | 12/2005 | Smit et al. | |
| 2006/0090711 | A1 | 5/2006 | Richards | |
| 2007/0272170 | A1 | 11/2007 | Milson et al. | |
| 2008/0067163 | A1 | 3/2008 | Axinte et al. | |
| 2008/0077214 | A1 | 3/2008 | Stalick | |
| 2008/0110414 | A1 | 5/2008 | Buehner | |
| 2008/0121192 | A1 | 5/2008 | Moy | |
| 2013/0106289 | A1 | 5/2013 | Beneski et al. | |
| 2014/0275824 | A1 | 9/2014 | Couse | |
| 2014/0358205 | A1 | 12/2014 | Robke et al. | |
| 2015/0276232 | A1 | 10/2015 | Wei | |
| 2017/0083018 | A1 | 3/2017 | Womble et al. | |
| 2017/0095206 | A1 | 4/2017 | Leib et al. | |
| 2017/0258629 | A1 | 9/2017 | Awasthi | |
| 2017/0367299 | A1 | 12/2017 | Mcdermott et al. | |
| 2018/0000353 | A1 | 1/2018 | Thieme et al. | |
| 2018/0014512 | A1 | 1/2018 | Arabani et al. | |
| 2019/0069513 | A1 | 3/2019 | Bevis | |
| 2019/0075758 | A1 * | 3/2019 | Ward | A01K 13/006 |
| 2019/0141951 | A1 * | 5/2019 | Coughlan | A01K 13/006 119/850 |
| 2019/0200577 | A1 | 7/2019 | Kath | |
| 2019/0223409 | A1 * | 7/2019 | Godfrey | A61F 7/08 |
| 2019/0374122 | A1 | 12/2019 | Kuenzi et al. | |
| 2020/0060545 | A1 * | 2/2020 | Maher | A61B 5/01 |
| 2020/0128792 | A1 * | 4/2020 | Tovornik | A01K 15/04 |
| 2020/0236906 | A1 * | 7/2020 | Koback | A01K 13/006 |
| 2020/0359605 | A1 * | 11/2020 | Maher | A01K 27/009 |

FOREIGN PATENT DOCUMENTS

| | | | |
|---|---|---|---|
| CN | 105532505 | A | 5/2016 |
| DE | 202012009870 | U1 | 1/2013 |
| DE | 102015009077 | A1 | 6/2017 |
| GB | 2440709 | A | 2/2008 |
| KR | 20110093175 | A | 8/2011 |
| WO | 2009128929 | A1 | 10/2009 |
| WO | 2016036114 | A1 | 3/2016 |
| WO | 2017216783 | A1 | 12/2017 |
| WO | 2019113256 | A1 | 6/2019 |

OTHER PUBLICATIONS

Sewport Support Team, "What is Mesh Fabric: Properties, How It's Made and Where," Sewport: 22 pages (Mar. 20, 2019) Retrieved on Nov. 28, 2022, retrieved from <URL: https://sewport.com/fabrics-directory/mesh-fabric#:-:text=In%20almost%20every%20case%20mesh,materials%20like%20polyester%20and%20nylon >.

* cited by examiner

PET HARNESS FOR MONITORING BODY TEMPERATURE AND PROVIDING COOLING OR HEATING

CROSS-REFERENCE TO RELATED APPLICATION

This application is a continuation of and claims priority to co-pending U.S. patent application Ser. No. 16/597,178, filed Oct. 9, 2019, which claims priority to U.S. Provisional Patent Application Ser. No. 62/743,960, filed Oct. 10, 2018, the disclosures of which are incorporated herein by reference in their entirety.

TECHNICAL FIELD

The subject matter herein generally relates to the field of heated and cooled wearable garments. The subject matter herein more particularly relates to systems, devices, and methods for monitoring a temperature of the wearer via a wearable garment, particularly a wearable harness for animals, and actively providing heating or cooling to the wearer.

BACKGROUND

Presently, a wearable harness is a popular, and often mandatory, device for attaching a leash and/or identification tags to control and/or identify an animal, such as a dog, while in public spaces, such as at parks, on streets, on hiking trails, and the like. During periods of hot and cold temperatures, it is known that the core temperature of an animal can become dangerously hot or cold due to exposure to the prevailing weather conditions. Similarly, it is not uncommon for humans working or performing other activities outdoors to become dangerously hot or cold. Many people engaging in such outdoor activities already wear specific harness-like garments, including, for example, reflective vests, hunting/fishing/hiking vests, and the like. As such, there exists a need at present to have a device and method of monitoring and maintaining a temperature of the wearer to be within a predefined acceptable range.

SUMMARY

A harness for heating and/or cooling a wearer of the harness is provided, the harness comprising an outer cover comprising a harness neck strap and a harness chest strap for securing the harness about the wearer of the harness; an internal surface comprising a breathable fabric material; at least one sensor attached to the harness chest strap; a thermal control device configured to cool or heat the wearer of the harness; a controller configured to activate the thermal control device; and a plurality of straps arranged over an external surface of the outer cover.

In some embodiments of the harness, the at least one sensor comprises a respiration sensor, a pulse sensor, and/or a temperature sensor.

In some embodiments of the harness, the temperature sensor is a cutaneous temperature sensor.

In some embodiments of the harness, the plurality of straps are configured to retain a power supply for the controller, the thermal control device, and/or the at least one sensor.

In some embodiments of the harness, the thermal control device is contained, at least in part, within a region of the harness neck strap.

In some embodiments of the harness, the breathable fabric material is a mesh-like material.

In some embodiments, the harness comprises one or more hollow spaces between the outer cover and the internal surface, through which air flow for the thermal control device is configured to be blown during operation, such that the air flow exit the hollow spaces through the mesh-like material of the inner surface to impinge upon a skin surface of the wearer of the harness.

In some embodiments of the harness, the outer cover comprises a layer that restricts airflow passing therethrough, so that substantially all of the air flow through the hollow spaces exits through the mesh-like material and onto the skin surface of the wearer of the harness.

In some embodiments of the harness, the thermal control device is configured to generate cooled air that can be ventilated onto the wearer of the harness through the mesh-like material of the internal surface via the hollow spaces.

In some embodiments of the harness, the thermal control device is a convective heater configured to generate heated air that can be ventilated onto the wearer of the harness through the mesh-like material of the internal surface via the hollow spaces.

In some embodiments of the harness, the thermal control device comprises one or more heating pads distributed about the harness to conduct heat to the wearer of the harness.

In some embodiments of the harness, the outer cover comprises a harness leg strap, and wherein a second at least one sensor is attached to the harness leg strap.

In some embodiments of the harness, the thermal control device is a cooling device comprising one or more of forced air cooling, evaporative cooling, and conductive cooling.

In some embodiments of the harness, the controller is configured to monitor a signal received from the at least one sensor, the signal comprising a vital parameter of the wearer of the harness.

In some embodiments of the harness, the vital parameter comprises one or more of a temperature, a respiration rate, a pulse rate, and a blood oxygen level.

In some embodiments of the harness, the controller is configured to compare the vital parameter against a predetermined threshold for the vital parameter and activate the thermal control device when the signal indicates that the vital parameter is beyond the predetermined threshold.

In some embodiments of the harness, the predetermined threshold is a default value based on a species of the wearer of the harness.

In some embodiments of the harness, the predetermined threshold is configured to be set by an instruction received from a remote input.

In some embodiments of the harness, the remote input is an input from an application on a mobile computing device.

In some embodiments of the harness, the controller is configured to activate the thermal control device based on an input from a user, wherein the input is configured to be received manually and/or remotely.

BRIEF DESCRIPTION OF THE DRAWING

A full and enabling disclosure of the present subject matter is set forth more in the remainder of the specification, including, for example, by referencing the accompanying example figures, in which.

DETAILED DESCRIPTION

This specification discloses systems and methods for monitoring the temperature and/or physical distress of a wearer and provides heating or cooling to the wearer (e.g., using a thermal control device) based on the parameters measured. While such systems and methods may be applied to and/or worn by any suitable animal, including humans, the following example embodiment is directed to a pet harness adapted for being worn by a pet and, specifically, by a dog.

Figure 1:
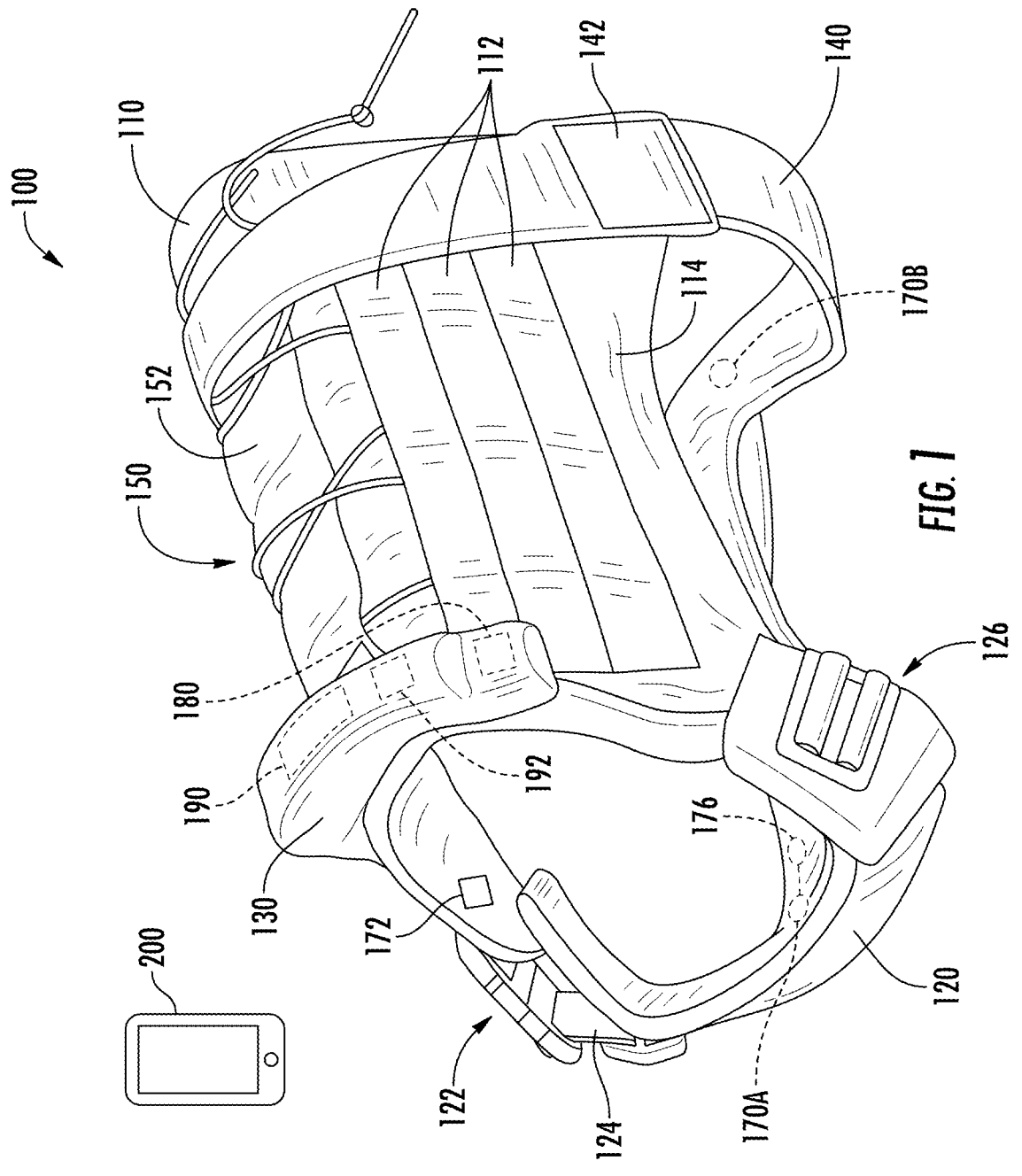
FIG. 1 shows an isometric view of an example embodiment of a wearable garment configured to heat and/or cool a wearer, in accordance with the disclosure herein.
Figure 2:
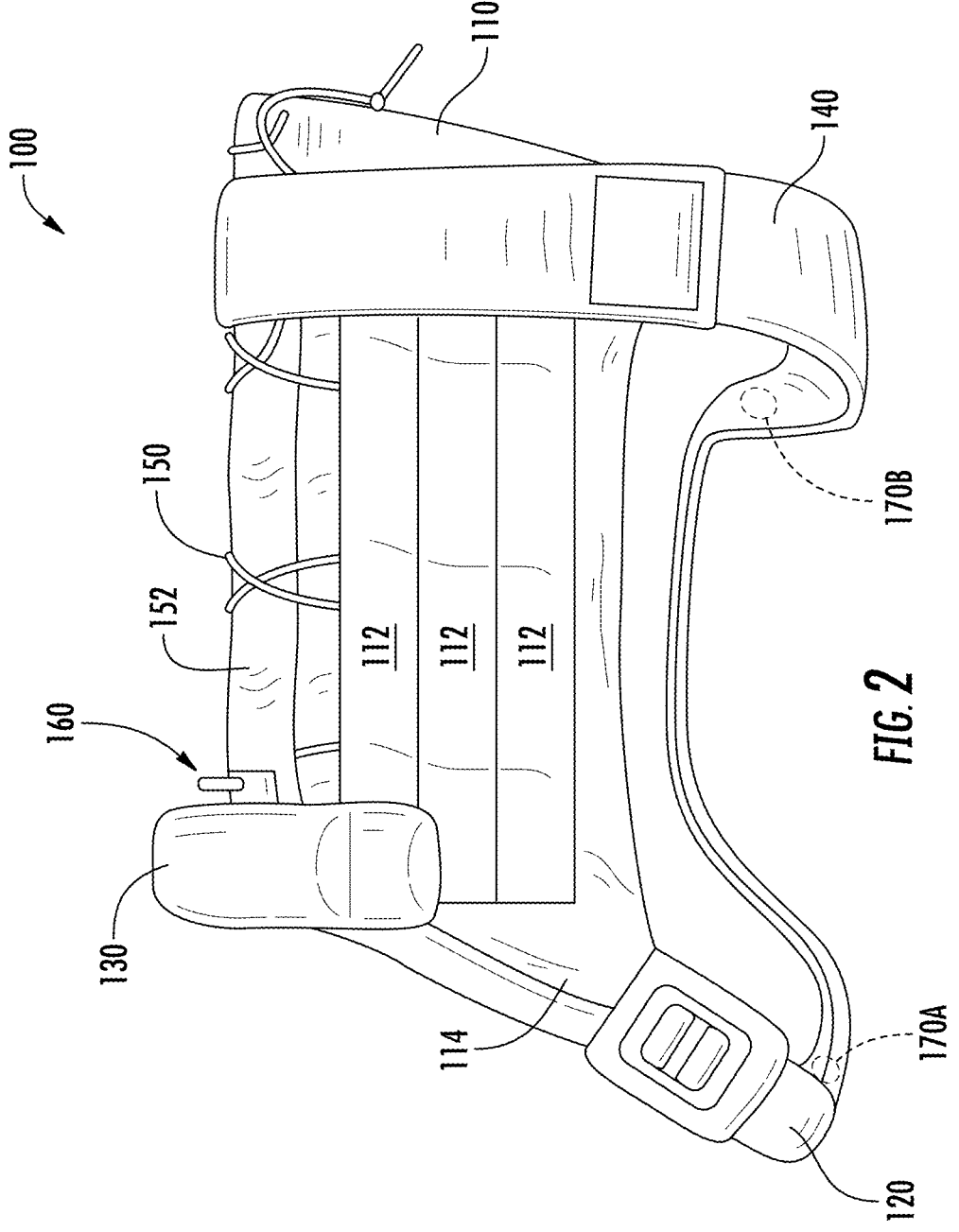
FIG. 2 shows a side view of the example embodiment of the wearable garment in FIG. 1, in accordance with the disclosure herein.
Figure 3:
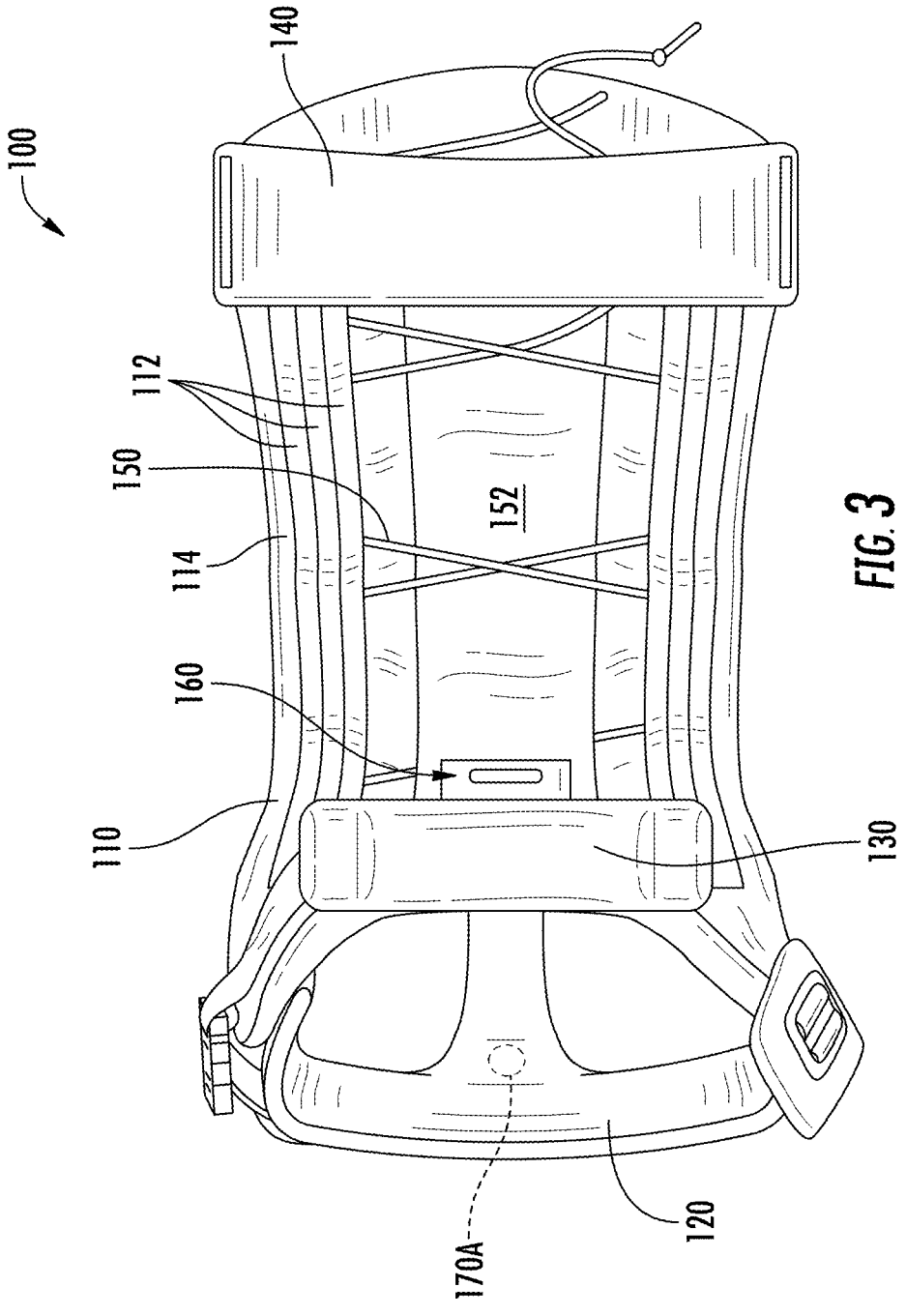
FIG. 3 shows a top view of the example embodiment of the wearable garment in FIG. 1, in accordance with the disclosure herein.

FIGS. 1-3 show various views of a harness, generally designated 100. The harness 100 has one or more sensors 170A, 170B capable of monitoring a wearer's (e.g., a dog's) body temperature or other vital signs (e.g., respiration rate, pulse rate, blood oxygen level, and the like). In some embodiments, it is advantageous for one or more of the sensors 170A, 170B to be temperature sensors that detect the wearer's body temperature cutaneously (e.g., by contact with the skin). In some embodiments, one or more of the sensors 170A, 170B is a thermistor, which may be particularly advantageous due to the increased accuracy compared to other types of temperature sensors, while the limited temperature ranges over which such thermistors exhibit such increased accuracy is acceptable due to the limited range of safe body temperatures. The illustration of the harness 100 shown in FIG. 1 is merely an example embodiment and is in no way to be construed as limiting the scope of the subject matter disclosed herein.

In some embodiments, one or more further sensors 172 may be provided, including, for example and without limitation, as a respiration sensor, a pulse sensor, a blood oxygen sensor, and the like. In some embodiments, the harness 100 comprises a transceiver 180, which can be wired but is preferably wireless. The transceiver 180 can be physically discrete (e.g., nonintegral) receiver and transmitter units or can be an integral unit with both send/receive functionality integrated therein. The transceiver 180 is configured to transmit information from the one or more sensors 170A, 170B, 172 to a remote location, which can be, for example, a server, a direct connection to a mobile device 200, or any other suitable transmission path and/or storage location. Similarly, the transceiver 180 is configured to receive commands/instructions from a remote location (e.g., a user on a mobile device or a web terminal). In some embodiments, the data transmitted may be sent periodically from the transceiver 180 to the remote location in an automatic manner, but in other embodiments it may be necessary for a query from the remote location to be received at the transceiver 180 to trigger the transmission of sensor data from the transceiver 180.

The harness 100 comprises an outer cover 110 that is sized to be approximately the same size (e.g., length, width, height, diameter, etc.) as the torso of the wearer of the harness 100. The outer cover 110 has, in some embodiments, an inner surface made of a breathable fabric, which can be, or have aspects of, mesh, netting, and/or perforations formed at least partially or entirely therethrough. The harness 100 is secured to the wearer by one or more of a harness chest strap 120, a harness neck strap 130, and a harness abdominal strap 140. In some embodiments, the harness abdominal strap 140 can be in the form of a harness leg strap, which can be in addition to, or as a replacement for, the harness abdominal strap 140 shown in FIGS. 1-3. A connector 160 to secure a lead (e.g., a leash) onto the harness 100 to control one or more aspects of the movement of the wearer can be located at any suitable position on the harness 100 that is readily accessible while the harness 100 is being worn by the wearer, including one or more of the harness neck strap 130, the outer cover 110, and the harness chest strap 120.

One or more of the harness chest strap 120, a harness neck strap 130, and a harness abdominal strap 140 can be in the form of flexible elastic bands that are fixedly attached to the outer cover 110. One or more of the harness chest strap 120, a harness neck strap 130, and a harness abdominal strap 140 can be in the form of flat straps that are secured to the outer cover 110 by, for example, hook-and-loop fasteners, or any suitable type of attachment (e.g., such as at attachment 142). In some embodiments, one or more of the harness chest strap 120, a harness neck strap 130, and a harness abdominal strap 140 can be a plurality of straps that can be in the form any of the flexible elastic bands and/or flat straps disclosed hereinabove. In any of the embodiments disclosed herein, the straps for one or more or all of the harness chest strap 120, a harness neck strap 130, and a harness abdominal strap 140 have a sufficient tensile strength and/or flexibility to retain a power source 190, such as an external battery pack, and/or a cooling unit (e.g., an ice pack or an amount of solid ice) in instances where direct cooling of the wearer is advantageous.

In the embodiment shown, the harness 100 comprises a plurality of cords 150, which are interlaced in a crossing pattern as shown in FIGS. 1-3. These cords 150 can be elastically deformable so that the length thereof can be altered (e.g., by stretching) so that the cords 150 can be used to secure, for example, a power source or cooling unit, as described above, respectively, or even a heater (e.g., an exothermic heater, an electric blanket-type heater, and the like) to the harness 100. In some embodiments, the harness 100 has a cover panel 152 that can be, for example, in the form of a pocket or sheet that can insulate the device secured by the cords 150 from the prevailing ambient conditions external to the harness 100. In some embodiments, the cover panel 152 can be used to shield the device secured by the cords 150 can be made of a reflective material to reflect incident light to decrease the temperature under the cover panel and of the wearer of the harness 100. In some embodiments, the cover panel 152 can be a vented material having a plurality of perforations formed therein that allow for the passage of air therethrough.

The sizing of the outer cover 110 can be customized to fit the wearer within a given range of sizes and/or dimensions by a set of straps 124 and buckles 122 that adjust an effective length of the harness chest strap 120, the harness neck strap 130, the harness leg strap 140, etc. In some embodiments, the cords 150 may also be adjusted to alter a fit of the harness 100 on the wearer. In some embodiments, the outer cover 110 comprises a rugged and wear-resistant fabric, including a nylon material. In some embodiments, the outer cover 110 comprises a plurality of panels 112 that can be made of any suitable material, including, for example, a perforated material to allow ventilation therethrough. In some embodiments, the panels 112 can be in the form of pockets into which cooled or heated devices (e.g., generally cylindrically-shaped and/or flexible ice packs and/or heaters) can be inserted to cool or heat, respectively, a wearer of the harness 100. In some embodiments, the panels 112 can be made of a reflective material to reflect incident light and increase the visibility of the wearer, while wearing the harness 100, by others. The outer cover 110 has a base layer 114, which can be for providing ventilation and/or insulation to the wearer of the harness 100.

In some embodiments, the harness neck strap 130 comprises a pocket or other at least partially enclosed region that contains a power source 190 (e.g., a battery, which can be rechargeable) and/or a cooling device, which can comprise a system for producing cooled air via a small electronic unit contained within this pocket/region. The internal surface of the base layer 114 of the harness 100 can include a "breathable" fabric, which can comprise a woven mesh material for allowing a ventilation of the wearer while using the harness 100. This mesh allows for ventilation and air flow through the harness directly on to the animal to provide convective cooling of the animal. In some embodiments, this convective cooling can be configured as an evaporative cooling system. In some embodiments, one or more hollow spaces, or pockets, is provided within the base layer 114, between the internal and outer surfaces thereof, to provide for ventilation (e.g., air movement) and also to allow for the placement of heat sources (e.g., heating pads) therein. The cooling device is configured to generate and distribute the cooled air throughout the hollow spaces in the base layer 114 of the harness 100 to directly impinge cooling air on the skin of the wearer through the mesh-like internal surface of the base layer 114 of the harness 100. In some embodiments, the cooling device comprises one or more air moving devices (e.g., fans, blowers, and the like) for moving the cooled air through the hollow space/internal pockets of the base layer 114 of the harness 100. The cooling devices can comprise aspects of one or more of convective cooling, evaporative cooling, or conductive cooling (e.g., directly applying a cold pack to the skin of the wearer).

In some other embodiments, the harness 100 comprises a heating system configured to generate and distribute heat to the wearer of the harness 100 similarly to the operation of the cooling system. As such, some embodiments will comprise primarily convective heating systems that are configured to distribute heated air through the hollow space/internal pockets of the base layer 114 of the harness 100 and to heat the skin of the wearer of the harness 100. In some embodiments, one or more heating pads (e.g., resistive heaters, exothermic heaters, or preheated materials) may be distributed about (e.g., internal and/or external to) the harness 100 and be powered by a battery pack (e.g., power source 190). Any such heating pads may be configured to operate at a suitably low voltage (e.g., 5V, 12V, 24V, 36V, and the like). In some embodiments, the heating pads may be configured to connect to a battery pack (e.g., power source 190) via a USB connector to receive power from the battery pack at approximately 5V. For example, a 10,400 mAh battery pack is capable of providing sufficient heat for a user for a duration of between approximately 3-12 hours, depending on the ambient temperature, the number of heating pads needed, the temperature to which the heating pads are set, etc. These heating pads can be positioned such that the heat produced thereby is distributed through the mesh-like internal surface of the base layer 114 of the harness 100 to impinge warmed air against the skin of the wearer.

The harness 100 comprises a controller 192 which can be connected to a power supply (e.g., power source 190). The controller 192 may comprise, for example, a processor, a memory, and a storage or any other suitable device. The controller 192 is typically connected electrically (e.g., via a wired connection) to each sensor 170A, 170B, 172 of the harness 100, but in some embodiments one or more sensors 170A, 170B, 172 can be in wireless communication with the controller 192. In instances where one or more sensors 170A, 170B, 172 are wirelessly connected to the controller 192, the sensors 170A, 170B, 172 can comprise a discrete power supply 176, which can be a power generation device. Such a power generation device can be of any suitable type, including, for example, kinetic generators that would generate power while the wearer of the harness 100 is moving. Any suitable wireless transmission type may be used, including, for example, Wi-Fi®, Bluetooth®, RFID, and the like. Any combination of wired and wireless sensors may be implemented for the sensors 170A, 170B, 172. In some embodiments, the controller 192 and/or one or more of the sensors 170A, 170B, 172 can be contained within the harness chest strap 120.

The controller 192 monitors the output(s) of the sensors 170A, 170B, 172 installed on the harness 100 and, depending on an operating mode selected, triggers an alert when the temperature, respiration rate, and/or pulse of the wearer, as detected by the sensors 170A, 170B, 172, exceeds predetermined threshold values and/or automatically triggers the heating or cooling features, depending on whether heating or cooling is needed in any given operational scenario and/or operating mode. These threshold values can be preset based on the type of wearer (e.g., dog, cat, pig, horse) of the harness 100 selected by an observer (e.g., a human). These threshold values can be further adjusted by the observer via a remote access application (e.g., a mobile application) to provide for earlier or delayed activation of the heating and/or cooling features. In some embodiments, the controller 192 may be configured to initially trigger an alert at a first warning sensor threshold, with the controller 192 being configured to only enable the heating or cooling features when a second critical sensor threshold is detected to avert physical harm to the wearer of the harness 100 from exposure to extreme temperatures. In embodiments where the first warning sensor threshold triggers an alert to an observer, the observer can manually trigger activation of the heating or cooling features on the harness 100, whether by a physical switch located on the harness or remotely (e.g., via the mobile application).

In some embodiments, the heating and cooling devices can be integrated within a single harness 100. In some other embodiments, the heating and cooling devices can be configured to be interchangeable, allowing for seasonal changes from heating-to-cooling or cooling-to-heating based on seasonal weather patterns.

While the embodiment of FIGS. 1-3 is provided merely for purposes of illustration, the features included in this example embodiment may be combined in any possible combination, as would be readily understood by persons having ordinary skill in the art.

The subject matter disclosed herein can be implemented in software in combination with hardware and/or firmware. For example, the subject matter described herein can be implemented in software executed by a processor or processing unit. In one exemplary implementation, the subject matter described herein can be implemented using a computer readable medium having stored thereon computer executable instructions that when executed by a processor of a computer control the computer to perform steps. Exemplary computer readable mediums suitable for implementing the subject matter described herein include non-transitory devices, such as disk memory devices, chip memory devices, programmable logic devices, and application specific integrated circuits. In addition, a computer readable medium that implements the subject matter described herein can be located on a single device or computing platform or can be distributed across multiple devices or computing platforms.

While at least one example embodiment of the invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a", "an" or "one" do not exclude a plural number, and the term "or" means either or both. Furthermore, characteristics or steps which have been described may also be used in combination with other characteristics or steps and in any order unless the disclosure or context suggests otherwise.

Other embodiments of the current invention will be apparent to those skilled in the art from a consideration of this specification or practice of the invention disclosed herein. Thus, the foregoing specification is considered merely exemplary of the current invention with the true scope thereof being defined by the following claims.

What is claimed is:

1. A dog harness for heating and/or cooling a dog wearing the dog harness, the dog harness comprising:
an outer cover comprising an internal surface having a breathable fabric material;
a harness neck strap that is attached to the outer cover and, when the dog harness is worn by the dog, is positioned over a top of a neck of the dog;
a harness chest strap that is attached to the outer cover and positioned below the neck and in front of front legs of the dog wearing the dog harness;
a harness abdominal strap that is attached to the outer cover and positioned behind the front legs and in front of rear legs of the dog wearing the dog harness;
at least one sensor directly on or in the harness chest strap and/or the harness abdominal strap;
a thermal control device configured to cool or heat the dog wearing the dog harness;
a controller configured to:
monitor a signal received from the at least one sensor, the signal comprising a vital parameter of the dog wearing the dog harness;
compare the vital parameter against a predetermined threshold for the vital parameter; and
activate the thermal control device when the signal indicates that the vital parameter is beyond the predetermined threshold;
a connector attached to the outer cover, wherein the connector is configured for attaching a lead, leash, or other tethering device to the dog harness for controlling movement of the dog wearing the dog harness;
wherein the harness neck strap, the harness chest strap, and the harness abdominal strap are configured for securing the dog harness onto the dog wearing the dog harness in a removable manner; and
wherein the harness neck strap and the harness chest strap form a hole, through which a head and at least a portion of the neck of the dog wearing the dog harness protrude while the dog is wearing the dog harness.

2. The dog harness of claim 1, wherein:
the at least one sensor comprises a respiration sensor, a pulse sensor, and/or a temperature sensor; and/or the vital parameter comprises one or more of a temperature of the dog wearing the dog harness, a respiration rate of the dog wearing the dog harness, a pulse rate of the dog wearing the dog harness, and a blood oxygen level of the dog wearing the dog harness.

3. The dog harness of claim 2, wherein the temperature sensor is a cutaneous temperature sensor.

4. The dog harness of claim 1, comprising a plurality of straps that are arranged over an external surface of the outer cover and configured to retain a power supply for the controller, the thermal control device, and/or the at least one sensor.

5. The dog harness of claim 1, wherein the thermal control device is contained, at least in part, within a region of the harness neck strap.

6. The dog harness of claim 1, wherein the harness neck strap is removably secured to the external surface of the outer cover.

7. The dog harness of claim 1, wherein the breathable fabric material is a mesh-like material, the dog harness comprising one or more hollow spaces between the outer cover and the internal surface, wherein the thermal control device is a convective heater configured to blow a heated air flow through the one or more hollow spaces during operation, such that the heated air flow exits the one or more hollow spaces through the mesh-like material of the internal surface to impinge upon a skin surface of the dog wearing the dog harness.

8. The dog harness of claim 1, wherein the thermal control device comprises one or more heating pads distributed about the dog harness to conduct heat to the dog wearing the dog harness.

9. The dog harness of claim 1, wherein:
the harness chest strap is in a form of a flat strap, at least one end of which comprises a removable attachment for securing the harness chest strap to the outer cover;
the harness abdominal strap is in a form of a flat strap, at least one end of which comprises a removable attachment for securing the harness abdominal strap to the outer cover; and
the at least one sensor comprises a first sensor, which is directly on or in the harness chest strap, and a second sensor, which is directly on or in the harness abdominal strap.

10. The dog harness of claim 9, comprising a further strap oriented parallel to a length of the dog wearing the harness that connects the harness abdominal strap to the harness chest strap.

11. The dog harness of claim 10, wherein the further strap is in a form of a flat strap extending between the harness chest strap and the harness abdominal strap.

12. The dog harness of claim 1, wherein the thermal control device is a cooling device configured for operation using conductive cooling.

13. The dog harness of claim 1, wherein the predetermined threshold is configured to be set by an instruction received from a remote input.

14. The dog harness of claim 13, wherein the remote input is an input from an application on a mobile computing device.

15. The dog harness of claim 1, wherein the controller is configured to activate the thermal control device based on an input from a user, wherein the input is configured to be received manually and/or remotely.

16. A dog harness for heating and/or cooling a dog wearing the dog harness, the dog harness comprising:

an outer cover comprising an internal surface having a breathable fabric material;

a harness neck strap that is attached to the outer cover and, when the dog harness is worn by the dog, is positioned over a top of a neck of the dog;

a harness chest strap that is attached to the outer cover and positioned below the neck and in front of front legs of the dog wearing the dog harness;

at least one sensor attached to, on, and/or in the harness chest strap;

a thermal control device configured to cool or heat the dog wearing the dog harness;

a controller configured to activate the thermal control device when a vital parameter of the dog wearing the dog harness is beyond a predetermined threshold;

wherein the harness neck strap and the harness chest strap are configured for securing the dog harness onto the dog wearing the dog harness in a removable manner; and wherein the harness neck strap and the harness chest strap form a hole, through which a head and at least a portion of the neck of the dog wearing the dog harness protrude while the dog is wearing the dog harness.

17. The dog harness of claim 16, comprising a harness abdominal strap that is attached to the outer cover and positioned behind the front legs and in front of rear legs of the dog wearing the dog harness.

18. A dog harness for heating and/or cooling a dog wearing the dog harness, the dog harness comprising:

an outer cover comprising a breathable fabric material;

a harness neck strap that is attached to the outer cover and, when the dog harness is worn by the dog, is positioned over a top of a neck of the dog;

a harness chest strap that is attached to the outer cover and positioned below the neck and in front of front legs of the dog wearing the dog harness;

at least one sensor attached to the harness chest strap;

a thermal control device configured to cool or heat the dog wearing the dog harness;

a controller configured to activate the thermal control device; and a plurality of straps arranged over an external surface of the outer cover;

wherein the harness neck strap and the harness chest strap are configured for securing the dog harness onto the dog wearing the dog harness; and wherein the harness neck strap and the harness chest strap form a hole, through which a head and at least a portion of the neck of the dog wearing the dog harness protrude while the dog is wearing the dog harness.

19. The dog harness of claim 18, comprising a harness abdominal strap that is attached to the outer cover and positioned behind the front legs and in front of rear legs of the dog wearing the dog harness.

20. The dog harness of claim 19, comprising a further strap oriented parallel to a length of the dog wearing the harness that connects the harness abdominal strap to the harness chest strap.

* * * * *